ORANGE TREE
Filed March 29, 1961 3 Sheets-Sheet 1
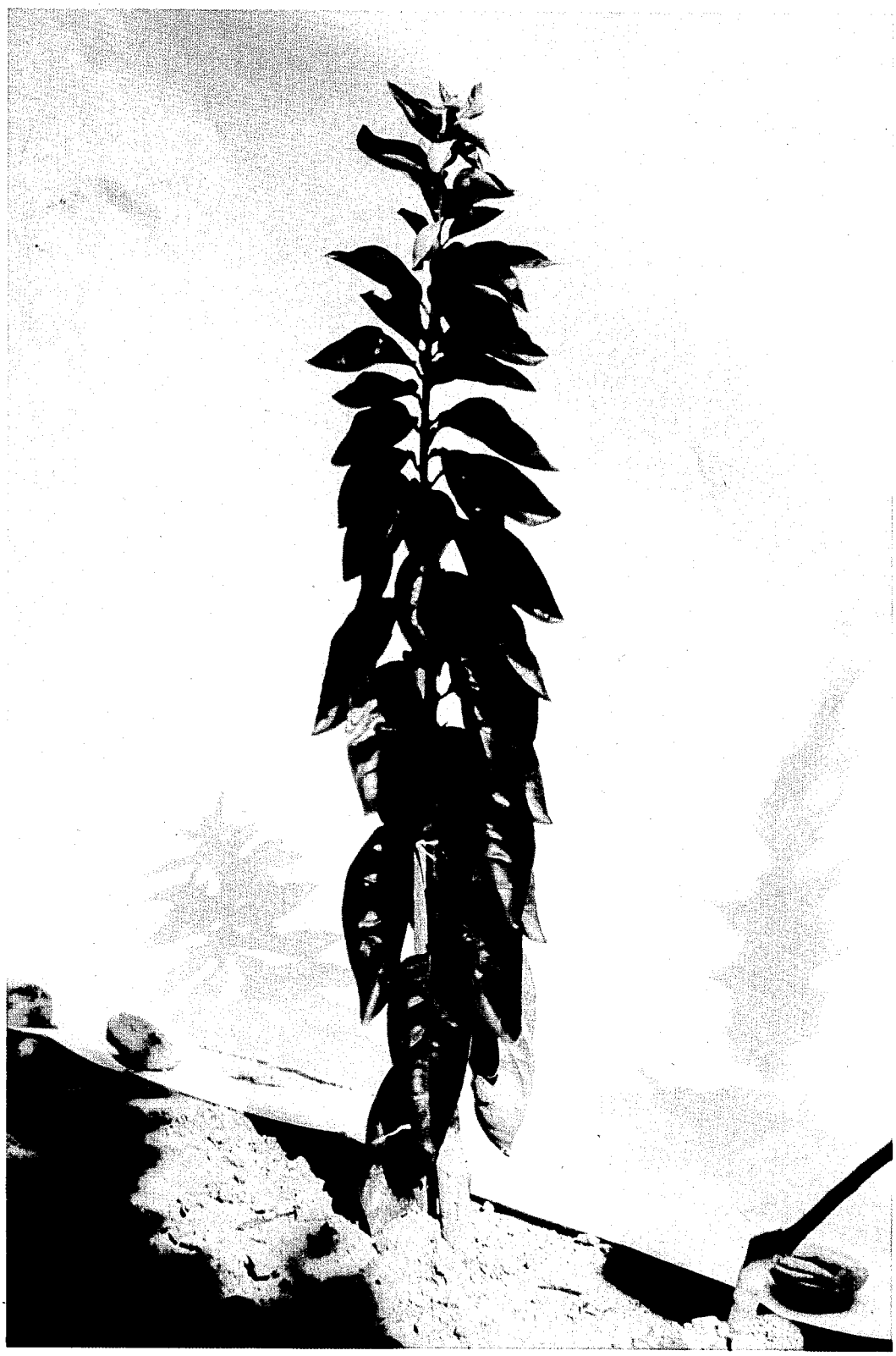

ORANGE TREE
Filed March 29. 1961 3 Sheets-Sheet 2
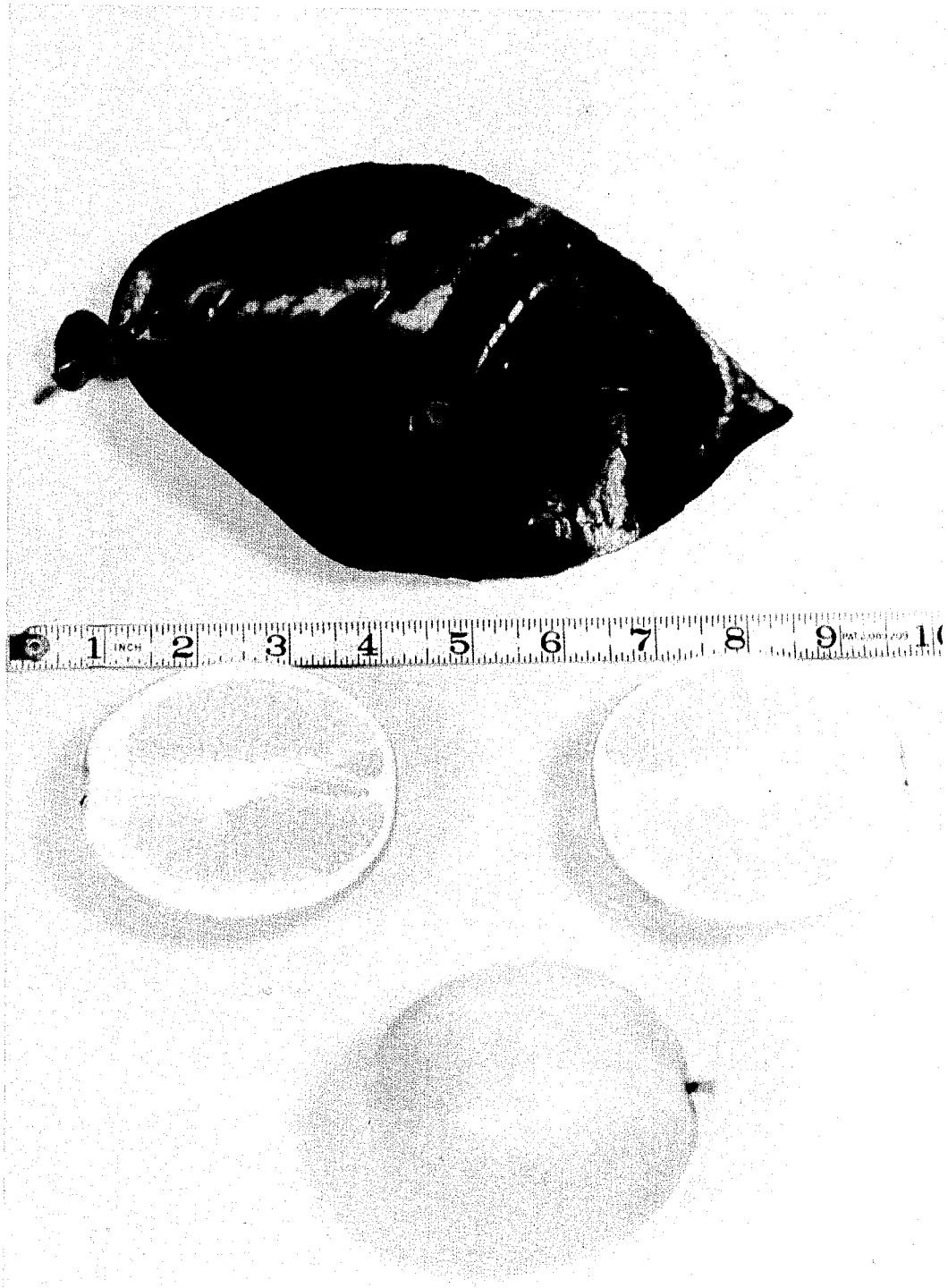

ORANGE TREE
Filed March 29, 1961 3 Sheets-Sheet 3
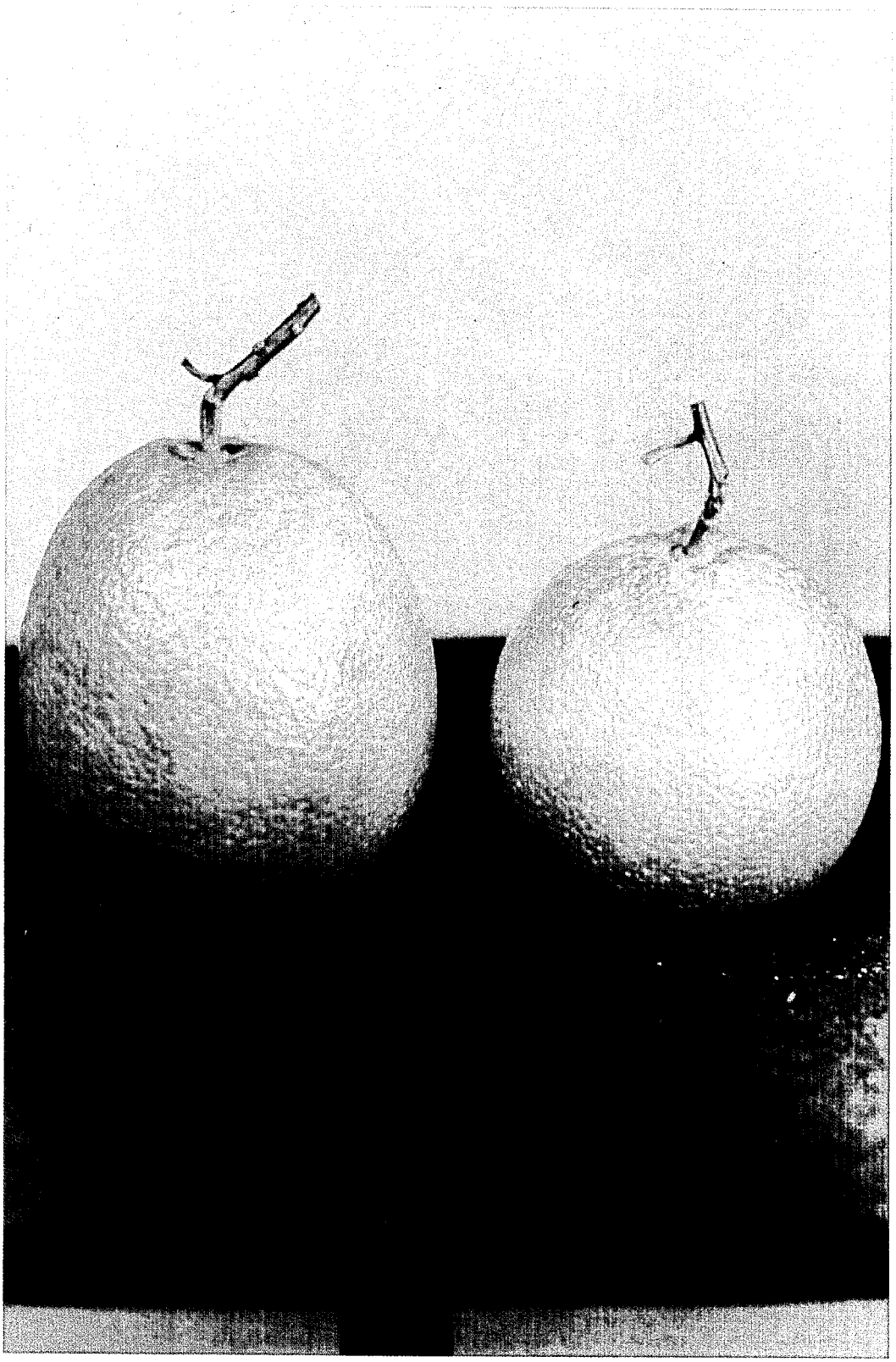

United States Patent Office

Plant Pat. 2,610
Patented Mar. 22, 1966

2,610
ORANGE TREE

Paul S. Gisler, P.O. Box 214; Clyde J. Bradley, 47 Granview Circle; and Joe Gisler, Jr., P.O. Box 499, all of Camarillo, Calif.

Filed Mar. 29, 1961, Ser. No. 99,327
1 Claim. (Cl. Plt.—45)

This invention relates to a new and distinct variety of orange tree and is characterized as to primary novelty by very vigorous growth, large foliage, and large fruit.

The orange tree results from a sport discovered on a single Valencia orange tree in a canyon north of Saticoy, California. We have reproduced the tree by removing a bud from the sport and placing it in a seedling of rough lemon root stock. The asexual reproduction of the instant variety of orange tree by budding has resulted in substantially seedless oranges of size one-third or so larger than a conventional Valencia orange (unpatented). Observations of the new tree may be made at Camarillo, California.

In the first of the accompanying drawings, there is shown an elevation in color of the orange tree itself and in the second drawing, a single leaf and a cross section of the fruit taken some three to four months before maturity. In the third drawing, there is shown on the left the size of one orange from the new tree compared with a conventional Valencia orange on the right.

Following is an outline description in greater detail of the distinct variety of orange tree of this invention:

*Plant*

Form: Tree.
Growth: Very vigorous.
Wood:
*New wood.*—Color—dark green. Bark—smooth.
*Old wood.*—Color—brown. Bark—smooth.
Foilage: Single leaf.
*Size.*—Very large.
*Quantity.*—Abundant.
*Color.*—New foliage: Upper side—dark green; under side—light green. Old foliage: Upper side—drak green; under side—light green.
*Shape.*—Oval, pointed.
*Texture.*—Upper side—glossy. Under side—smooth.
*Ribs and veins.*—Ordinary.
*Edge.*—Smooth.
*Leaf stem color.*—Green.
Fruit: Very good quality. Grows in large clusters. Variety is fertile with its own pollen.
*Form.*—Ovoid or oblong.
*Aspect.*—Smooth.
*Color at maturity.*—Yellow-orange.
*Size at maturity.*—Very large.
*Seeds.*—Very few.
Blooming habit: Blooms once profusely about springtime when Valencia oranges bloom.

As will be evident from the third drawing, the fruit on the tree described herein is definitely larger than the conventional Valencia orange. Further, its somewhat oval or pear shape is evident. The tree itself is coarser with larger leaves than the Valencia tree and while some seeds may be present in the fruit, there are considerably fewer than in the conventional Valencia orange.

The most distinguishing characteristic of the fruit is its relatively large size compared to the fruit from a standard Valencia orange tree. In this respect, actual measurements of 20 oranges selected at random from the parent tree of this invention were made and compared with 20 oranges selected at random from a standard Valencia orange tree of comparable nutritional value. The results of these measurements are as follows.

From parent tree of present invention:

[Diameter in inches]

| | | | | | | | |
|---|---|---|---|---|---|---|---|
| 1 | 3.21 | 6 | 3.18 | 11 | 3.23 | 16 | 3.27 |
| 2 | 3.20 | 7 | 3.13 | 12 | 3.18 | 17 | 3.27 |
| 3 | 3.15 | 8 | 3.28 | 13 | 3.21 | 18 | 3.23 |
| 4 | 3.22 | 9 | 3.18 | 14 | 3.29 | 19 | 3.18 |
| 5 | 3.20 | 10 | 3.18 | 15 | 3.31 | 20 | 3.09 |

The average length of these oranges is 3.75 inches.

From standard Valencia of comparable nutritional value:

[Diameter in inches]

| | | | | | | | |
|---|---|---|---|---|---|---|---|
| 1 | 2.50 | 6 | 2.56 | 11 | 2.55 | 16 | 2.62 |
| | 2.56 | 7 | 2.60 | 12 | 2.45 | 17 | 2.70 |
| 3 | 2.80 | 8 | 2.75 | 13 | 2.65 | 18 | 2.71 |
| 4 | 2.75 | 9 | 2.60 | 14 | 2.85 | 19 | 2.69 |
| 5 | 3.00 | 10 | 3.00 | 15 | 2.73 | 20 | 2.81 |

The average length of these oranges is 2.60 inches.

The tree and its fruit herein described may vary in slight detail due to climatic or soil conditions under which the variety is grown.

What is claimed is:

A new and distinct variety of orange tree substantially as shown and described, characterized particularly as to novelty by the unique combination of very vigorous growth, very large foliage, and fruit in size one-third or so larger than ordinary Valencia oranges, said fruit having very few seeds.

No references cited.

ABRAHAM G. STONE, *Primary Examiner.*